United States Patent [19]

Yonese et al.

[11] Patent Number: 4,629,800
[45] Date of Patent: Dec. 16, 1986

[54] FLUORAN COMPOUNDS

[75] Inventors: Naoki Yonese, Nishinomiya; Masayuki Omatsu, Yao; Mitsuru Kondo, Kawabe, all of Japan

[73] Assignee: Kanzaki Paper Manufacturing Co., Ltd., Tokyo, Japan

[21] Appl. No.: 706,885

[22] Filed: Mar. 1, 1985

[30] Foreign Application Priority Data

Mar. 9, 1984 [JP] Japan .................................. 59-45797
Mar. 10, 1984 [JP] Japan .................................. 59-46353
Mar. 12, 1984 [JP] Japan .................................. 59-47951

[51] Int. Cl.$^4$ .......................................... C07D 407/04
[52] U.S. Cl. ........................................ 549/226; 106/21; 346/221
[58] Field of Search ................... 549/226; 106/21; 346/221

[56] References Cited

U.S. PATENT DOCUMENTS

| 3,825,561 | 7/1974 | Akamatsu et al. | 549/226 |
| 4,104,437 | 8/1978 | Vincent et al. | 549/226 X |
| 4,364,999 | 12/1982 | Motohashi et al. | 549/226 X |
| 4,444,591 | 4/1984 | Kawai et al. | 549/226 X |
| 4,535,348 | 8/1985 | Iwakura et al. | 346/221 |

FOREIGN PATENT DOCUMENTS 47-34422 11/1972 Japan .
78886 5/1984 Japan .
120654 7/1984 Japan .
2141727 1/1985 United Kingdom .

Primary Examiner—Richard L. Raymond
Attorney, Agent, or Firm—Wenderoth, Lind & Ponack

[57] ABSTRACT

Fluoran compounds of the structural formula:

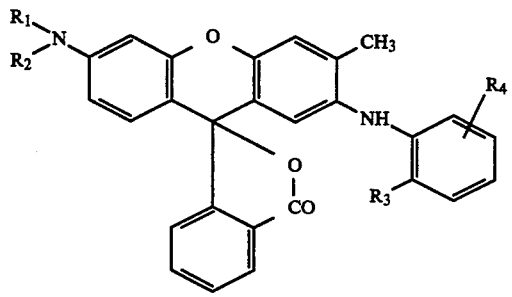

wherein $R_1$ is propyl or butyl, $R_2$ is an alkyl of from one to four carbon atoms, $R_3$ is methyl or ethyl, and $R_4$ is hydrogen or methyl are particularly suitable for use in providing high quality pressure, heat or electrothermal sensitive recording sheets containing a color former in operative association with an electron-accepting substance.

2 Claims, No Drawings

FLUORAN COMPOUNDS

BACKGROUND OF THE INVENTION

This invention relates to novel fluoran derivatives and to the use thereof as electron donative color forming substances in pressure sensitive, heat sensitive and electrothermal sensitive recording sheets.

There have been proposed hitherto various kinds of recording (copying) systems for transmitted information wherein a color forming reaction between a colorless or light color basic chromogenic material and an electron accepting organic or inorganic material is utilized, and mechanical, heat, electric or light energy serves as a medium. Among them there are included a pressure sensitive copying sheet, a heat sensitive recording sheet, an electrothermal sensitive recording sheet, an ultrasonic recording sheet, an electron beam recording sheet, an electrostatic recording sheet and a photosensitive recording sheet as described in JAPAN TAPPI vol. 30, pp. 411–421 and 463–470 (1976).

There are found various proposals for the utilization of those kinds of recording (copying) systems in photosensitive printing compositions, typewriter ribbons, ball-point pen ink, crayon and stamp ink.

In such recording systems, utilizing the color reaction between an electron donating color forming material (hereinafter referred to as "color former") and an electron accepting color developing material (hereinafter referred to as "acceptor"), images showing various hues may be obtained by using various kinds of color formers. There is now an increased demand for recording systems by which black color images capable of being reproducible for copies may be obtained. Theoretically, images of substantially black color may be obtained by using a mixture of various color formers which will develop into the respective hues of different colors such as red, blue, yellow and green. The utilization of a mixture of various color formers for obtaining a black color has, however, a disadvantage that the once developed black color images can not be maintained for a long period of time because the color formers employed are respectively different in their color developing speeds and their color fastnesses against light, temperature and moisture. In consequence, some attempts have been made hitherto to obtain images of substantially black color with the use of a single color former. However, there has not yet been found any such color former capable of developing a substantially black color image that always satisfies all of the requirements for stability before its color development, its color developing speed, its color fastness, its color hue, its color image as developed and its production costs.

The primary object of this invention is to provide novel fluoran derivatives.

Another object of this invention is to provide novel fluoran derivatives which are useful as color formers in various recording sheets.

Another object of this invention is to provide novel color formers for use in recording sheets in which the color images as developed assume a substantially deep-black color and have a good light resistance.

A further object of this invention is to provide novel color formers for use in heat sensitive or electrothermal sensitive recording sheets which give substantially no fogging on the record materials to which they are applied.

A still further object of this invention is to provide novel color formers for use in pressure sensitive recording sheets which possess a good and instant color developability.

It is also included among the objects of this invention to provide an improved moisture resistant recording sheet in which a fluoran derivative as a new compound is used as a color former and the color images as developed thereby possess a good light resistance and assume a substantially deep-black color which is suitable for reproduction of copies.

SUMMARY OF THE INVENTION

The novel fluoran derivatives according to the invention have the structural formula:

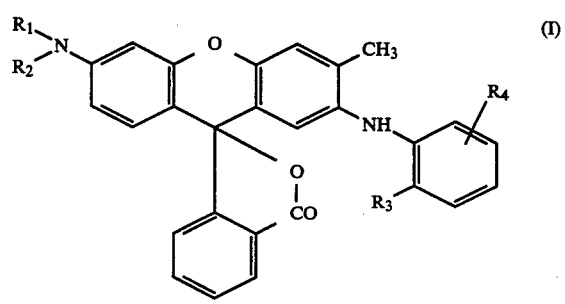

wherein $R_1$ is propyl or butyl, $R_2$ is an alkyl of from one to four carbon atoms, $R_3$ is methyl or ethyl, and $R_4$ is hydrogen or methyl.

The fluoran derivatives of the above structural formula (I) may be used as color formers in various recording sheets including pressure sensitive recording sheets, heat sensitive recording sheets and electrothermal sensitive recording sheets. The compounds according to this invention produce a color of substantially deep-black upon contact with an acceptor. The color images as developed with the use of said fluoran derivatives as color formers possess a good light resistance and maintain clear color hues once produced for a long period of time.

DETAILED DESCRIPTION OF THE INVENTION

The compounds represented by the structural formula (I) are illustrated by particular compounds represented by the following formulas:

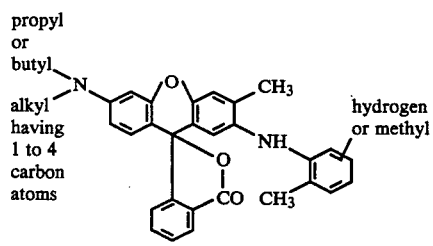

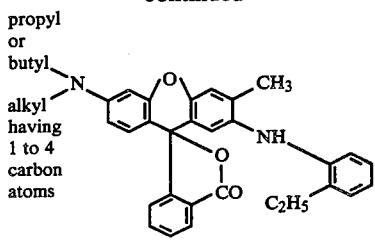

These compounds according to this invention which are represented by the structural formula (I) may be prepared representatively by the manner as hereunder shown:

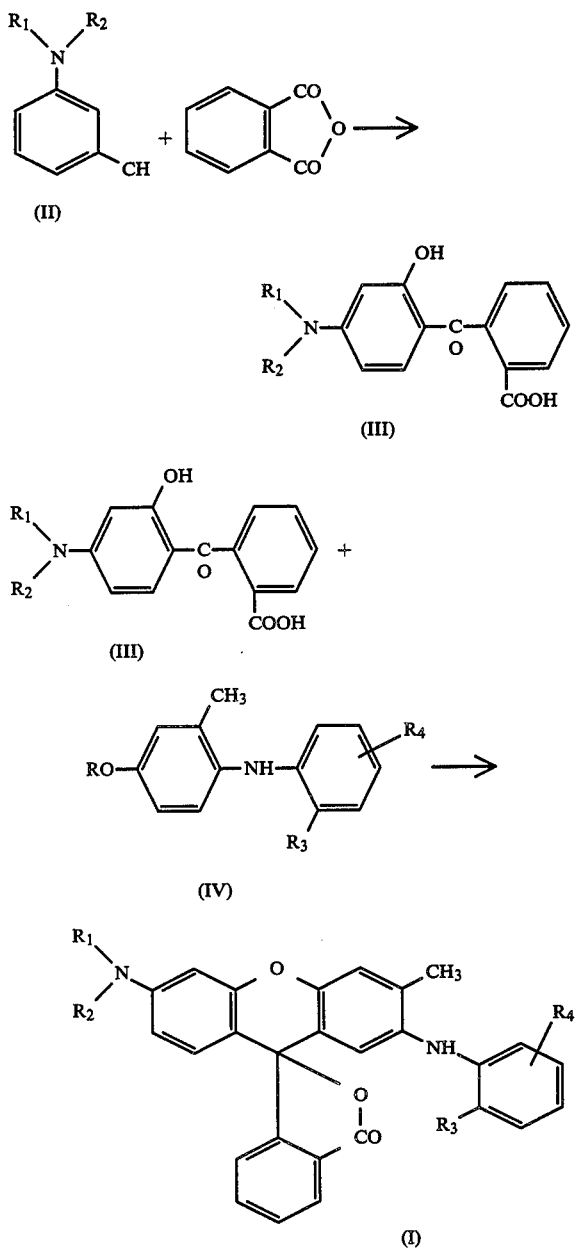

wherein R is hydrogen or alkyl having 1 to 4 carbon atoms, $R_1$, $R_2$, $R_3$ and $R_4$ are the same as defined before, respectively.

In this manner, an m-substituted aminophenol derivative represented by the above structural formula (II) is reacted with phthalic anhydride to produce the 2-(2-hydroxy-4-substituted amino)benzoyl benzoic acid derivative represented by the above structural formula (III). This is then reacted with a 4-hydroxydiphenylamine derivative represented by the above structural formula (IV) to produce an objective compound of the structural formula (I).

In both the first reaction between the m-substituted aminophenol derivative represented by the structural formula (II) and phthalic anhydride and the second reaction between the 2-(2-hydroxy-4-substituted amino)benzoyl benzoic acid derivative represented by the structural formula (III) and the 4-hydroxydiphenylamine derivative represented by the structural formula (IV), it is advantageous to use an appropriate condensing agent. And, in either of the two reactions, the condensing agent is preferred to be Friedel-Crafts type catalyst such as sulfuric acid; phosphorus pentoxide; phosphoric acid; polyphosphoric acid; anhydrous metal halide such as anhydrous tin chloride, anhydrous zinc chloride, anhydrous aluminum chloride, anhydrous tin bromide, anhydrous zinc bromide, anhydrous aluminum bromide and anhydrous iron bromide; phosphorus trichloride; phosphorus tribromide; phosphorus pentachloride; phosphorus pentabromide; anhydrous boron trifluoride; and hydrofluoric acid. Among these, the most preferred condensing agent is sulfuric acid.

As the solvent to be used in either of the two reactions, carbon disulfide, monochlorobenzene, trichlorobenzene, nitrobenzene, nitromethane, nitroethane or a mixture of two or more these solvents are preferable. Sulfuric acid, the most preferred condensing agent, also functions as a good solvent.

In said second reaction, when R is an alkyl having 1 to 4 carbon atoms in the 4-hydroxy-diphenylamine derivative represented by the structural formula (IV), there will be sometimes produced a triarylmethane derivative represented by the following formula:

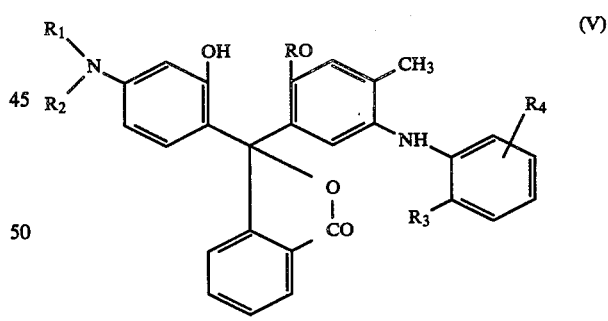

wherein R is alkyl having 1 to 4 carbon atoms, $R_1$, $R_2$, $R_3$ and $R_4$ are the same as defined above.

In that case, said triarylmethane derivative may be converted into an objective compound of the structural formula (I), for example, in the following manner. That is: first, if necessary, it is separated from the reaction mixture by an appropriate filtration means, then heated to a temperature of 50° C. to 100° C. wherein the pH value of the aqueous system is adjusted to higher than 9.0 with the use of a basic substance such as sodium hydroxide, potassium hydroxide and the like.

In order to increase the yield of the compounds represented by the formula (I) according to this invention, in the foregoing manner an organic solvent such as acetone, benzene, toluene or xylene may be added to the aqueous reaction mixture. Hydrophobic organic solvents such as benzene, toluene and xylene are effective also in prevention of by-products from being formed.

The compounds having the structural formula (I) provided according to this invention are colorless or pale and stable materials. Upon contact with acceptors, they develop a hue of substantially deep black color. The record color images which are obtained with the use of these compounds possess a characteristic that even when exposed to the sun light the color tones once obtained can be maintained for a long period of time. In addition, when applied to a pressure sensitive recording sheet, record images excelling especially in instant color developability are obtained. Further, when applied to a heat sensitive recording sheet, record images with no texture fogginess and excelling in color developability and storageability even under high moisture atmospheric condition are obtained.

The fluoran derivatives of the prior art which have similar structural formulas to those represented by the structural formula (I) according to this invention and which are capable of being color formers in pressure sensitive copying sheets and heat sensitive recording sheets are known from U.S. Pat. No. 4,330,473, GB No. 2,002,801A and Japanese Patent Publication No. 15445/1976.

It has now been ascertained that the fluoran derivatives represented by the structural formula (I) according to this invention are notably superior to these known counterparts in the following points; a significant color developing density is given upon tight contact with acceptors, and heat sensitive recording sheets produced with the use of 4,4'-isopropylidenediphenol, benzoyl 4-hydroxybenzoate or the like as an acceptor are increased in their color developing sensitivity and are less accompanied with a texture fogginess.

Thus, the fluoran derivatives represented by the structural formula (I) according to this invention are colorless or light colored basic chromogenic materials which have the excellent characteristics as above stated and which achieve superior effects especially when used in various recording sheets in which the color reaction with an acceptor is utilized. The fluoran derivatives represented by the structural formula (I) according to this invention may be used either alone or as a mixture of two or more.

The acceptors to be employed are selected appropriately in accordance with the kinds of recording sheets desired. For example, in a recording sheet such as pressure sensitive recording sheet, heat sensitive recording sheet and electrothermal sensitive recording sheet, those which function as Bronsted acid or Lewis acid are preferred to be used. Examples of these acceptors are: inorganic acceptors such as acid clay, activated clay, attapulgite, bentonite, colloidal silica, aluminum silicate, magnesium silicate, zinc silicate, tin silicate, calcined kaolin and talc; organic acceptors such as aliphatic carboxylic acids, e.g., oxalic acid, maleic acid, tartaric acid, citric acid, succinic acid and stearic acid, aromatic carboxylic acids, e.g., benzoic acid, p-tert-butylbenzoic acid, phthalic acid, gallic acid, salicylic acid, 3-isopropylsalicylic acid, 3-phenylsalicylic acid, 3-cyclohexylsalicylic acid, 3,5-di-tert-butylsalicylic acid, 3-methyl-5-benzylsalicylic acid, 3-phenyl-5-($\alpha,\alpha$-dimethylbenzyl)salicylic acid, 3,5-di($\alpha$-methylbenzyl)salicylic acid and 2-hydroxyl-1-benzyl-3-naphthoic acid, phenolic compounds, e.g., 4-tert-octylphenol, 4,4'-sec-butylidenediphenol, 4-phenylphenol, 4,4'-isopropylidenediphenol, 4,4'-cyclohexylidenediphenol, 4,4'-dihydroxydiphenylsulfide, 4,4'-thiobis(6-tert-butyl-3-methylphenol), 4,4'-dihydroxydiphenylsulfone, 4-hydroxybenzophenone, 2,4-dihydroxybenzophenone, 2,4,4'-trihydroxybenzophenone, 2,2',4,4'-tetrahydroxybenzophenone, dimethyl 4-hydroxyphthalate, methyl 4-hydroxybenzoate, ethyl 4-hydroxybenzoate, propyl 4-hydroxybenzoate, sec-butyl 4-hydroxybenzoate, pentyl 4-hydroxybenzoate, phenyl 4-hydroxybenzoate, benzyl 4-hydroxybenzoate, tolyl 4-hydroxybenzoate, chlorophenyl 4-hydroxybenzoate, phenylpropyl 4-hydroxybenzoate, phenethyl 4-hydroxybenzoate, p-chlorobenzyl 4-hydroxybenzoate and p-methoxybenzyl 4-hydroxybenzoate, phenol resins, e.g., p-phenylphenol-formaldehyde resin and p-butylphenol-acetylene resin; salts of the above organic acceptors with polyvalent metals such as zinc, magnesium, aluminium, calcium, titanium, manganese, tin and nickel; and inorganic acid such as hydrogen halide, e.g., hydrogen chloride, hydrogen bromide and hydrogen iodide, boric acid, silicic acid, phosphoric acid, sulfuric acid, nitric acid, perchloric acid and halides of aluminium, zinc, nickel, tin, titanium, boron and the like.

Typical recording sheets of various kinds for which the fluoran derivatives represented by the structural formula (I) according to this invention are used will be hereunder further explained.

The fluoran derivatives represented by the structural formula (I) according to this invention can be used for those pressure sensitive recording sheets of various forms such as are disclosed in U.S. Pat. Nos. 2,505,470, 2,505,471, 2,505,489, 2,548,366, 2,712,507, 2,730,456, 2,730,457, 3,418,250, 3,924,027 and 4,010,038.

The fluoran derivatives of this invention to be applied to these pressure sensitive recording sheets can be used either alone or in combination.

Generally, the production of a pressure sensitive recording sheet using of the fluoran derivatives according to this invention is practiced in the following manner. First, one or more of the fluoran derivatives according to this invention is dissolved in a solvent or a mixture of two or more solvents in a known manner to produce a solution. Usable as the solvent therein are, for example, synthetic oil such as alkylated naphthalene, alkylated diphenyl, alkylated diphenylmethane and alkylated terphenyl, vegetable oil such as cotton seed oil and castor oil, animal oil or mineral oil. The solution may additionally contain one or more basic dyes such as triphenylmethane lactones, spiropyrans, fluorans, diphenylmethanes and Leucomethylene Blue.

The solution thus obtained is dispersed in a binder to form a dispersion. Alternatively, said solution is encapsulated in microcapsules according to known microencapsulation method such as coacervation method, interfacial polymerization method and in-situ polymerization method, then dispersed in a binder to form a dispersion. The dispersion thus prepared is applied onto a support such as paper sheet, plastic sheet, resin coated paper sheet, etc. to thereby obtain a pressure sensitive recording sheet.

Among the pressure sensitive recording sheets provided according to this invention there are included various types; a top sheet in which to one side of the support is applied said dispersion, a middle sheet in which to one side of the support is applied an acceptor coating composition containing as the main component an acceptor and to the other side of the support is applied said dispersion, and a so-called self-contained type copying sheet in which to one side of the support is applied a mixture of the microcapsule dispersion and the acceptor, or first the microcapsule dispersion is applied successively followed by a coating of the aforesaid acceptor coating composition.

Since the amount of the fluoran derivative according to this invention to be used will vary depending upon the form of the pressure sensitive recording sheet to be produced, the encapsulation method to be employed, the constituents of the coating composition including various auxiliary agents to be used, the coating method etc., the amount will be determined appropriately in accordance with the related conditions concerned.

In any case, the use of the fluoran derivatives represented by the structural formula (I) according to this invention as a color former in known various pressure sensitive sheets brings about production of a pressure sensitive recording sheet capable of forming a record image which excells in color developability.

The fluoran derivatives according to this invention can be utilized also for various kinds of heat sensitive recording sheets such as those disclosed in Japanese Patent Publications Nos. 3680/1969, 27880/1969, 14039/1970, 43830/1973, 69/1974, 70/1974 and 20142/1977. For the heat sensitive recording sheets to be obtained, the use of one or more of the fluoran derivatives according to this invention as a color former provides the ability to produce a record image having the excellent characteristics as above described. Typically, the heat sensitive recording sheet according to the present invention may be produced by applying a coating composition, which has been prepared by dispersing fine particles of one or more of the fluoran derivatives according to this invention and fine particles of an acceptor in a medium containing a binder in which it is dissolved or dispersed, onto an appropriate support such as paper sheet, plastic film, synthetic paper sheet, woven fabric sheet or mold. The quantitative proportion of the acceptor versus the color former of which the principal ingredient is the fluoran derivative according to this invention respectively to be used in the recording layer of the heat sensitive recording sheet to be provided according to this invention is not particularly limited. However, it is common to use 1 to 50 parts by weight of the acceptor versus 1 part by weight of the color former. And using 2 to 10 parts by weight of the acceptor versus 1 part by weight of the color former is preferred.

In order to achieve the aim of improving the color developability, matting the surface of the recording layer and improving the writingability, inorganic metal compounds such as oxides, hydroxides and carbonates respectively of polyvalent metals, and/or inorganic pigments in an amount of 0.1 to 5 parts by weight, preferably, 0.2 to 2 parts by weight versus 1 part by weight of the acceptor to be used may be added to the coating composition.

Further, if necessary, the recording layer may contain dispersing agents, ultraviolet ray absorbing agents, heat fusible materials, antifoaming agent, fluorescent dye, coloring dyes and other relevant auxiliary agents.

As above described, the heat sensitive recording sheet to be provided according to this invention is, generally, produced by applying to a support a coating composition in which fine particles of the fluoran derivative represented by the structural formula (I) and fine particles of an acceptor are dispersed. As an alternative, it is possible to prepare two separate coating compositions, i.e., one containing said fluoran derivative and the other containing said acceptor and apply them to the support one by one.

The application of such coating composition to the support may also be carried out by known impregnation or sizing methods.

As for the methods for the preparation of the coating composition and its application to the support in this invention there is not any particular limitation, and any relevant method in addition to those above described may also be employed.

The amount of the coating composition containing the fluoran derivative represented by the structural formula (I) and the acceptor to be applied to the support is generally of 2 to 12 g/cm$^2$.

Usable as the binder are, for example, various starches, celluloses, proteins, gum arabic, polyvinyl alcohol, salts of styrene-maleic anhydride copolymer, styrene-butadiene copolymer emulsions, salts of vinyl acetate-maleic anhydride copolymer and salts of polyacrylic acid.

The electrothermal recording sheet provided according to this invention may be produced according to known methods such as those disclosed in Japanese Laid-Open Patent Publications Nos. 11,344 of 1974 and 48,930 of 1975. Usually, the record sheet of this type may be produced, either by applying to a support such as a paper sheet, a coating composition namely a dispersion containing an electroconductive material, a color former essentially consisting of the fluoran derivative according to this invention, an acceptor and a binder, or by first applying an electroconductive material to the support to thereby form an electroconductive layer thereon, and then applying to the electroconductive layer previously formed another coating composition namely a dispersion containing a color former essentially consisting of the fluoran derivative according to this invention, an acceptor and a binder. When the fluoran derivative and/or the acceptor as used are not fusible at the suitable temperature of from 70° to 120° C., their sensitivity against Joule heat may be adjusted by the use of an appropriate heat fusible material together with them.

PREFERRED EMBODIMENTS OF THE INVENTION

The following examples serve to illustrate the invention in more detail but the invention is not limited to the examples. Unless otherwise indicated, parts and % signify parts by weight and % by weight, respectively.

EXAMPLES OF SYNTHESIS

1. Synthesis of 3-N-ethyl-N-butylamino-6-methyl-7-(2,3-xylidino)fluoran

In 100 ml of concentrated sulfuric acid, 34.1 g of 2-(2-hydroxy-4-N-ethyl-N-butylamino)benzoylbenzoic acid and 26.5 g of 2,2′,3′-trimethyl-4-methoxydiphenylamine were reacted at room temperature for 24 hours. After the reaction was completed, the reaction product was poured in 1000 ml of ice water and the solid substance consequently precipitated therein was separated by filtration. The solid substance was dispersed in 500 ml of water, alkalined to pH 11 with sodium hydroxide aqueous solution at room temperature, then mixed with 300 ml of toluene and heated at 85° C. for 3 hours. The toluene layer formed was separated, subjected to reduced pressure distillation to remove toluene therefrom, then recrystallized from ethyl alcohol to afford 43.4 g of a colorless needle-like crystalline product having a melting point of 150° to 151° C. with the yield of 81.6%, which was identified to be 3-N-ethyl-N-butylamino-6-methyl-7-(2,3-xylidino)fluoran. This compound instantaneously formed a color of black on contact with silica gel.

2. Synthesis of 3-N-methyl-N-propylamino-6-methyl-7-(2,4-xylidino)fluoran

In 100 ml of concentrated sulfuric acid, 31.3 g of 2-(2-hydroxy-4-N-methyl-N-propylamino)benzoylbenzoic acid and 25 g of 2,2',4'-trimethyl-4-hydroxydiphenylamine were reacted at room temperature for 17 hours. After the reaction was completed, the reaction product was poured in 1000 ml of ice water and alkalined to pH 9.0 with 20% sodium hydroxide aqueous solution at room temperature. The solid substance consequently precipitated therein was separated by filtration, washed with distilled water and dried. The dried substance was then recrystallized from benzene to afford 39.8 g of a colorless crystalline product having a melting point of 164° to 167° C. with the yield of 79%, which was identified to be 3-N-methyl-N-propylamino-6-methyl-7-(2,4-xylidino)fluoran.

This compound instantaneously formed a color of black on contact with silica gel.

3. Synthesis of 3-N-ethyl-N-butylamino-6-methyl-7-orthotoluidinofluoran

In 100 ml of concentrated sulfuric acid, 34.1 g of 2-(2-hydroxy-4-N-ethyl-N-butylamino)benzoylbenzoic acid and 25.0 g of 2,2'-dimethyl-4-methoxybiphenylamine were reacted at room temperature for 24 hours. After the reaction was completed, the reaction product was poured in 1000 ml of ice water, alkalined to pH 11 with 20% sodium hydroxide aqueous solution at room temperature, then after 300 ml of acetone was added, refluxed for 3 hours. After removing acetone therefrom, the resulting crystalline precipitate was separated by filtration, washed with distilled water, then recrystallized from chloroform-ethanol to afford 43.3 g of a colorless needle-like crystalline product having a melting point of 199° to 200° C. with the yield of 83.6%, which was identified to be 3-N-ethyl-N-butylamino-6-methyl-7-orthotoluidinofluoran. This compound instantaneously formed a color of black on contact with silica gel.

4. Synthesis of 3-N-ethyl-N-butylamino-6-methyl-7-(2,5-xylidino)fluoran

The procedures of Example 1 were repeated except that 2,2',5'-trimethyl-4-methoxydiphenylamine instead of 2,2',3'-trimethyl-4-methoxydiphenylamine was used, to afford 40.8 g of a colorless crystalline product having a melting point of 233° to 234.5° C. with the yield of 76.7% (recrystallized from chloroform-ethanol), which was identified to be 3-N-ethyl-N-butylamino-6-methyl-7-(2,5-xylidino)fluoran.

This compound instantaneously formed a color of black on contact with silica gel.

5. Synthesis of 3-N,N-dibutylamino-6-methyl-7-(2,3-xylidino)fluoran

In 100 ml of concentrated sulfuric acid, 36.9 g of 2-(2-hydroxy-4-N,N-dibutylamino)benzoylbenzoic acid and 26.5 g of 2,2',3'-trimethyl-4-methoxydiphenylamine were reacted at room temperature for 24 hours. After the reaction was completed, the reaction product was poured in 1000 ml of ice water and the solid substance consequently precipitated was separated by filtration. The separated solid substance was dispersed in 500 ml of distilled water to obtain a dispersion, the dispersion was alkalined to pH 11 with sodium hydroxide aqueous solution at room temperature, then mixed with 300 ml of toluene and heated at 85° C. for 3 hours. The toluene layer consequently formed was separated. The separated material was subjected to reduced pressure distillation to remove toluene therefrom then the solid substance was recrystallized from propylalcohol to afford a colorless needle-like crystalline product having a melting point of 163° to 164° C. with the yield of 81.6%, which was identified to be 3-N,N-dibutylamino-6-methyl-7-(2,3-xylidino)fluoran.

This compound instantaneously formed a color of black on contact with silica gel.

6. Synthesis of 3-N,N-dibutylamino-6-methyl-7-(2,4-xylidino)fluoran

In 100 ml of concentrated sulfuric acid, 36.9 g of 2-(2-hydroxy-4-N,N-dibutylamino)benzoylbenzoic acid and 25.0 g of 2,2',4'-trimethyl-4-hydroxydiphenylamine were reacted at room temperature for 17 hours. After the reaction was completed, the reaction product was poured in 1000 ml of ice water, alkalined to pH 9 with 20% sodium hydroxide aqueous solution at room temperature. The solid substance consequently precipitated therein was separated by filtration. The solid substance was then washed with distilled water and dried. The dried substance was then recrystallized from propylalcohol to afford 36.9 g of a colorless product having a melting point of 160° to 161° C. with the yield of 65.9%, which was identified to be 3-N,N-dibutylamino-6-methyl-7-(2,4-xylidino)fluoran.

This compound instantaneously formed a color of black on contact with silica gel.

7. Synthesis of 3-N,N-dibutylamino-6-methyl-7-(2,5-xylidino)fluoran

In 100 ml of concentrated sulfuric acid, 36.9 g of 2-(2-hydroxy-4-N,N-dibutylamino)benzoylbenzoic acid and 26.5 g of 2,2',5'-trimethyl-4-ethoxydiphenylamine were reacted at room temperature for 24 hours. After the reaction was completed, the reaction product was poured in 1000 ml of ice water and the solid substance consequently precipitated therein was separated by filtration. The separated solid substance was dispersed in 500 ml of distilled water to obtain a dispersion. The dispersion was alkalined to pH 11 with sodium hydroxide aqueous solution, mixed with 300 ml of acetone then refluxed for 3 hours. After removing acetone therefrom, the resulting crystalline solid substance was separated by filtration, washed with distilled water then recrystallized from ethylalcohol to afford 48.0 g of a colorless needle-like crystalline product having a melting point of 136° to 137° C. with the yield of 85.7%, which was identified to be 3-N,N-dibutylamino-6-methyl-7-(2,5-xylidino)fluoran.

This compound instantaneously formed a color of black on contact with silica gel.

8. Synthesis of 3-N,N-dipropylamino-6-methy-7-(2,3-xylidino)fluoran

The procedures of Example 5 were repeated except that 34.1 g of 2-(2-hydroxy-4-N,N-dipropylamino)benzoylbenzoic acid was used instead of 2-(2-hydroxy-4-N,N-dibutylamino)benzoylbenzoic acid, to afford 42.2 g of a colorless crystalline product having a melting point of 158° to 159° C. with the yield of 79.3% (recrystallized from chloroform-ethanol), which was identified to be 3-N,N-dipropylamino-6-methyl-7-(2,3-xylidino)-fluoran.

This compound instantaneously formed a color of black on contact with silica gel.

9. Synthesis of 3-N,N-dipropylamino-6-methyl-7-orthotoluidinofluoran

In 100 ml of concentrated sulfuric acid, 34.1 g of 2-(2-hydroxy-4-N,N-dipropylamino)benzoylbenzoic acid and 25.0 g of 2,2'-dimethyl-4-methoxydiphenylamine were reacted at room temperature for 24 hours. After the reaction was completed, the reaction product was poured in 1000 ml of ice water, alkalined to pH 11 with sodium hydroxide aqueous solution at room temperature, mixed with 300 ml of acetone then refluxed for 3 hours. The crystalline precipitate which resulted after removing acetone therefrom was separated by filtration, washed with distilled water then recrystallized from chloroform-ethanol to afford 41.1 g of a colorless needle-like crystalline product having melting point of 178.5° to 180° C. with the yield of 79.3%, which was identified to be 3-N,N-dipropylamino-6-methyl-7-orthotoluidinofluoran.

This compound instantaneously formed a color of black on contact with silica gel.

10. Synthesis of 3-N,N-dibutylamino-6-methyl-7-orthotoluidinofluoran

In 100 ml of concentrated sulfuric acid, 36.9 g of 2-(2-hydroxy-4-N,N-dibutylamino)benzoylbenzoic acid and 25.0 g of 2,2'-dimethyl-4-methoxydiphenylamine were reacted at room temperature for 24 hours. After the reaction was completed, the reaction product was poured in 1000 ml of ice water, alkalined to pH 11 with 20% sodium hydroxide aqueous solution at room temperature, mixed with 300 ml of acetone then refluxed for 3 hours. The crystalline precipitate which resulted after removing acetone therefrom was separated by filtration, the precipitate was washed with distilled water then recrystallized from chloroform-ethanol to afford 44.8 g of a colorless needle-like crystalline product having a melting point of 157° to 159° C. with the yield of 82.1%, which was identified to be 3-N,N-dibutylamino-6-methyl-7-orthotoluidinofluoran.

This compound instantaneously formed a color of black on contact with silica gel.

11. Synthesis of 3-N,N-dipropylamino-6-methyl-7-(2,4-xylidino)fluoran

In 100 ml of concentrated sulfuric acid, 34.1 g of 2-(2-hydroxy-4-N,N-dipropylamino)benzoylbenzoic acid and 25.0 g of 2,2',4'-trimethyl-4-hydroxydiphenylamine were reacted at room temperature for 17 hours. After the reaction was completed, the reaction product was poured in 1000 ml of ice water, alkalined to pH 9 with 20% sodium hydroxide aqueous solution at room temperature then the solid substance consequently precipitated therein was separated by filtration. The separated solid substance was washed with distilled water, dried then recrystallized from propylalcohol to afford 39.2 g of a colorless crystalline product having a melting point of 196° to 197° C. with the yield of 73.7%, which was identified to be 3-N,N-dipropylamino-6-methyl-7-(2,4-xylidino)fluoran.

This compound instantaneously formed a color of black on contact with silica gel.

12. Synthesis of 3-N,N-dibutylamino-6-methyl-7-orthoethylanilinofluoran

In 100 ml of concentrated sulfuric acid, 36.9 g of 2-(2-hydroxy-4-N,N-dibutylamino)benzoylbenzoic acid and 26.5 g of 2-methyl-4-methoxy-2'-ethyldiphenylamine were reacted at room temperature for 24 hours. After the reaction was completed, the reaction product was poured in 1000 ml of ice water and the solid substance consequently precipitated therein was separated by filtration. The separated solid substance was dispersed in 500 ml of distilled water to obtain a dispersion. The dispersion was alkalined to pH 11 with sodium hydroxide aqueous solution, mixed with 300 ml of toluene then heated at 85° C. for 3 hours. The toluene layer consequently formed therein was separated, after subjected to reduced pressure distillation to remove toluene, the resulting was recrystallized from ethylalcohol to afford 46.3 g of a colorless crystalline product having a melting point of 172° to 173° C. with the yield of 82.7%, which was identified to be 3-N,N-dibutylamino-6-methyl-7-orthoethylanilinofluoran.

This compound instantaneously formed a color of black on contact with silica gel.

13. Synthesis of 3-N-ethyl-N-butylamino-6-methyl-7-orthoethylanilinofluoran

In 100 ml of concentrated sulfuric acid, 34.1 g of 2-(2-hydroxy-4-N-ethyl-N-butylamino)benzoylbenzoic acid and 26.5 g of 2-methyl-4-methoxy-2'-ethyldiphenylamine were reacted at room temperature for 24 hours. After the reaction was completed, the reaction product was poured in 1000 ml of ice water and the solid substance consequently precipitated therein was separated by filtration. The separated solid substance was dispersed in 500 ml of distilled water to obtain a dispersion. The dispersion was alkalined to pH 11 with sodium hydroxide aqueous solution, mixed with 300 ml of acetone then refluxed for 3 hours. The crystalline precipitate resulted after removing acetone therefrom was separated, washed with distilled water then recrystallized from isopropylalcohol to afford 42.9 g of a colorless crystalline product having a melting point of 132° to 133° C. with the yield of 80.6%, which was identified to be 3-N-ethyl-N-butylamino-6-methyl-7-orthoethylanilinofluoran.

This compound instantaneously formed a color of black on contact with silica gel.

14. Synthesis of 3-N,N-dipropylamino-6-methyl-7-orthoethylanilinofluoran

The procedures of Example 12 were repeated except that 34.1 g of 2-(2-hydroxy-4-N,N-dipropylamino)-benzoylbenzoic acid was used instead of 2-(2-hydroxy-4-N,N-dibutylamino)benzoylbenzoic acid, to afford 44.0 g of a colorless crystalline product having a melting point of 146° to 147° C. with the yield of 82.7% (recrystallized from acetone-methanol), which was identified to be 3-N,N-dipropylamino-6-methyl-7-orthoethylanilinofluoran.

This compound instantaneously formed a color of black on contact with silica gel.

EXAMPLES OF COMPARATIVE TEST (1) A heat sensitive recording sheet was made in the following manner with the use of 3-N-ethyl-N-butylamino-6-methyl-7-(2,3-xylidino)fluoran obtained in Example of Synthesis 1 (hereinafter referred to as "Compound 1").

(i) Preparation of Liquid A
A composition composed of:

| | |
|---|---|
| Compound 1 | 5 parts |
| stearic acid amide | 1 part |
| 2% aqueous solution of hydroxyethylcellulose | 25 parts | was passed through a sand grinder and pulverized to an average size of 2 microns.

(ii) Preparation of Liquid B

A composition composed of:

| | |
|---|---|
| 4,4'-isopropylidene diphenol | 50 parts |
| stearic acid amide | 10 parts |
| 2% aqueous solution of hydroxyethylcellulose | 250 parts | was passed through a sand grinder and pulverized to an average size of 2 microns.

(iii) Preparation of Liquid C

A composition composed of:

| | |
|---|---|
| Liquid A | 62 parts |
| Liquid B | 310 parts |
| ultrafine particles of silicic anhydride ("Syloid 244" manufactured by Fuji-Davidson Chemical Company) | 25 parts |
| 20% aqueous solution of a salt of styrene-maleic anhydride copolymer | 175 parts |
| zinc stearate | 5 parts |
| water | 100 parts | was prepared by thoroughly mixing the materials above mentioned to form a coating composition.

The coating composition was applied onto a base sheet of 50 g/m$^2$ in weight in an amount of 6 g/m$^2$ on dry basis to obtain a heat sensitive recording sheet (hereinafter referred to as "No. A").

Likewise, 3-N-methyl-N-propylamino-6-methyl-7-(2,4-xylidino)fluoran obtained in Example of Synthesis 2 (hereinafter referred to as "Compound 2"), 3-N-ethyl-N-butylamino-6-methyl-7-orthotoluidinofluoran obtained in Example of Synthesis 3 (hereinafter referred to as "Compound 3"), 3-N-ethyl-N-butylamino-6-methyl-7-(2,5-xylidino)fluoran obtained in Example of Synthesis 4 (hereinafter referred to as "Compound 4"), 3-N,N-dibutylamino-6-methyl-7-(2,3-xylidino)fluoran obtained in Example of Synthesis 5 (hereinafter referred to as "Compound 5"), 3-N,N-dibutylamino-6-methyl-7-(2,4-xylidino)fluoran obtained in Example of Synthesis 6 (hereinafter referred to as "Compound 6"), 3-N,N-dibutylamino-6-methyl-7-(2,5-xylidino)fluoran obtained in Example of Synthesis 7 (hereinafter referred to as "Compound 7"), 3-N,N-dipropylamino-6-methyl-7-(2,3-xylidino)fluoran obtained in Example of Synthesis 8 (hereinafter referred to as "Compound 8"), 3-N,N-dipropylamino-6-methyl-7-orthotoluidinofluoran obtained in Example of Synthesis 9 (hereinafter referred to as "Compound 9"), 3-N,N-dibutylamino-6-methyl-7-orthotoluidinofluoran obtained in Example of Synthesis 10 (hereinafter referred to as "Compound 10") and 3-N,N-dipropylamino-6-methyl-7-(2,4-xylidino)fluoran obtained in Example of Synthesis 11 (hereinafter referred to as "Compound 11") were used to obtain respective heat sensitive recording sheets (hereinafter referred to as "No B", "No C", "No D", "No E", "No F", "No G", "No H", "No I", "No J" and "No K", respectively).

For comparative purpose, also likewise the known 3-diethylamino-6-methyl-7-(2,4-xylidino)fluoran (U.S. Pat. No. 4,330,473)[hereinafter referred to as "Compound B-1"] and 3-N-ethyl-N-n-hexylamino-6-methyl-7-p-toluidinofluoran (GB No. 2,002,801A) [hereinafter referred to as "Compound B-2"] were used to obtain respective heat sensitive recording sheets (hereinafter referred to as "No L" and "No M" respectively).

With the use of these heat sensitive recording sheets No A through No M, the following tests were carried out.

Tests of Color Developability on the Heat Sensitive Recording Sheets

The heat sensitive recording sheets No A to No M prepared as described above were pressed with a pressure of 4 kg/cm$^2$ for 5 seconds on plates heated to 80° C., 90° C., 100° C. and 120° C. respectively. The sheets were tested for their developed hues, color densities and texture fogginesses by means of a Macbeth Reflection Densitometer.

The heat sensitive recording sheets which were color-developed at 120° C. were stored at 50° C. with 90% RH for 24 hours then measured their record densities by means of a Macbeth Reflection Densitometer for the evaluation of their moisture resistances.

The recording layers of the heat sensitive recording sheets which were color-developed at 120° C. were exposed to sunlight for the evaluation of their light resistances.

The light resistance was determined by the time length (hr.) until a color change was visually apparent.

The results are as shown in Table 1.

TABLE 1

| Heat Sensitive Recording Sheet | | | Color Forming Ability | | | | | | |
|---|---|---|---|---|---|---|---|---|---|
| Fluoran Derivative | Recording Sheet | Hue | Temperature | | | | Fogging Characteristics | Moisture Resistance | Light Resistance (hr) |
| | | | 80° C. | 90° C. | 100° C. | 120° C. | | | |
| Present Compound | | | | | | | | | |
| Compound 1 | No A | Reddish Black | 1.01 | 1.25 | 1.30 | 1.33 | 0.03 | 1.07 | 7 |
| Compound 2 | No B | Greenish Black | 0.98 | 1.20 | 1.28 | 1.31 | 0.03 | 1.08 | 6–7 |
| Compound 3 | No C | Reddish Black | 1.00 | 1.25 | 1.31 | 1.33 | 0.03 | 1.06 | 7 |
| Compound 4 | No D | Greenish Black | 0.99 | 1.24 | 1.30 | 1.33 | 0.03 | 1.07 | 6–7 |
| Compound 5 | No E | Reddish Black | 0.98 | 1.21 | 1.28 | 1.32 | 0.02 | 1.05 | 7–8 |
| Compound 6 | No F | Greenish Black | 0.96 | 1.20 | 1.28 | 1.31 | 0.02 | 1.03 | 7 |
| Compound 7 | No G | Black | 0.96 | 1.21 | 1.29 | 1.32 | 0.03 | 1.05 | 7 |
| Compound 8 | No H | Reddish Black | 0.95 | 1.20 | 1.28 | 1.31 | 0.03 | 1.10 | 7–8 |
| Compound 9 | No I | Reddish Black | 0.97 | 1.20 | 1.28 | 1.31 | 0.03 | 1.07 | 7 |

TABLE 1-continued

| Heat Sensitive Recording Sheet | | | Color Forming Ability | | | | | | |
|---|---|---|---|---|---|---|---|---|---|
| Fluoran Derivative | Recording Sheet | Hue | Temperature | | | | Fogging Characteristics | Moisture Resistance | Light Resistance (hr) |
| | | | 80° C. | 90° C. | 100° C. | 120° C. | | | |
| Compound 10 | No J | Reddish Black | 0.99 | 1.21 | 1.30 | 1.32 | 0.02 | 1.03 | 7–8 |
| Compound 11 | No K | Greenish Black | 0.94 | 1.21 | 1.28 | 1.31 | 0.03 | 1.09 | 7 |
| Known Compound | | | | | | | | | |
| Compound B-1 | No L | Greenish Black | 0.46 | 0.94 | 1.15 | 1.30 | 0.05 | 1.03 | 4 |
| Compound B-2 | No M | Greenish Black | 0.94 | 1.20 | 1.28 | 1.31 | 0.08 | 0.60 | 6–7 |

From the results of the above comparative tests, it was ascertained that the heat sensitive recording sheets in which the fluoran derivatives represented by the structural formula (I) were used are totally superior to those in which known fluoran derivatives were used.

(2) A heat sensitive recording sheet was made in the following manner with the use of 3-N,N-dibutylamino-6-methyl-7-orthoethylanilinofluoran obtained in Example of Synthesis 12 (hereinafter referred to as "Compound 12").

(i) Preparation of Liquid A

A composition composed of:

| Compound 12 | 5 parts |
|---|---|
| stearic acid amide | 1 part |
| 2% aqueous solution of hydroxyethylcellulose | 25 parts | was passed through a sand mill and pulverized to an average size of 2 microns.

(ii) Preparation of Liquid B

A composition composed of:

| 4,4'-isopropylidene diphenol | 50 parts |
|---|---|
| stearic acid amide | 10 parts |
| 2% aqueous solution of hydroxyethylcellulose | 250 parts | was passed through a sand mill and pulverized to an average size of 2 microns.

(iii) Preparation of Liquid C

A composition composed of:

| Liquid A | 62 parts |
|---|---|
| Liquid B | 310 parts |
| ultrafine particles of silicic anhydride ("Syloid 244" manufactured by Fuji-Davidson Chemical Company) | 25 parts |
| 20% aqueous solution of a salt of styrene-maleic anhydride copolymer | 175 parts |
| zinc stearate | 5 parts |
| water | 100 parts | was prepared by thoroughly mixing the materials above mentioned to form a coating composition.

The coating composition was applied onto a base sheet of 50 g/m² in weight in an amount of 6 g/m² on dry basis to obtain a heat sensitive recording sheet (hereinafter referred to as "No N").

Likewise, 3-N-ethyl-N-butylamino-6-methyl-7-orthoethylanilinofluoran obtained in Example of Synthesis 13 (hereinafter referred to as "Compound 13") and 3-N,N-dipropylamino-6-methyl-7-orthoethylanilinofluoran obtained in Example of Synthesis 14 (hereinafter referred to as "Compound 14") were used to obtain respective heat sensitive recording sheets (hereinafter referred to as "No O" and "No P" respectively).

For comparative purpose, also likewise known 3-N,N-diethylamino-6-methyl-7-orthotoluidinofluoran (Japanese Patent Publication No. 17490/1974)[hereinafter referred to as "Compound B-3"] was used to obtain a heat sensitive recording sheet (hereinafter referred to as "No Q"). Together with this, the sheet No M which was prepared in Example of Comparative Test (1) was employed for the same purpose.

With the use of these heat sensitive recording sheets No N through No Q and No M, the following tests were carried out.

Tests of Color Developability on the Heat Sensitive Recording Sheets

The heat sensitive recording sheets No N to No Q prepared as described above and the heat sensitive recording sheet No M were pressed with a pressure of 4 kg/cm² for 5 seconds on plates heated to 80° C., 90° C., 100° C. and 120° C. respectively. The sheets were tested for their developed hues, color densitites and texture fogginesses by means of a Macbeth Reflection Densitometer.

The heat sensitive recording sheets which were color-developed at 120° C. were stored at 50° C. with 90% RH for 24 hours then measured their record densities by means of a Macbeth Reflection Densitometer for the evaluation of their moisture resistances.

The recording layers of the heat sensitive recording sheets which were color-developed at 120° C. were exposed to sunlight for the evaluation of their light resistances.

The light resistance was determined by the time length (hr.) until a color change was visually apparent.

The results are as shown in Table 2.

TABLE 2

| Heat Sensitive Recording Sheet | | Color Forming Ability | | | | | Fogging Characteristics | Moisture Resistance | Light Resistance (hr) |
|---|---|---|---|---|---|---|---|---|---|
| Fluoran Derivative | Recording Sheet | Hue | Temperature | | | | | | |
| | | | 80° C. | 90° C. | 100° C. | 120° C. | | | |
| Present Compound | | | | | | | | | |
| Compound 12 | No N | Reddish Black | 0.97 | 1.21 | 1.30 | 1.33 | 0.02 | 1.06 | 7–8 |
| Compound 13 | No O | Reddish Black | 1.02 | 1.23 | 1.31 | 1.33 | 0.03 | 1.10 | 7 |
| Compound 14 | No P | Reddish Black | 0.95 | 1.20 | 1.28 | 1.31 | 0.03 | 1.07 | 7 |
| Known Compound | | | | | | | | | |
| Compound B-3 | No Q | Reddish Black | 0.41 | 0.86 | 1.14 | 1.28 | 0.04 | 1.05 | 4–5 |
| Compound B-2 | No M | Greenish Black | 0.94 | 1.20 | 1.28 | 1.31 | 0.08 | 0.60 | 6–7 |

From the results of the above comparative tests, it was ascertained that the heat sensitive recording sheets in which the fluoran derivatives represented by the structural formula (I) were used are totally superior to those in which known fluoran derivatives were used.

EXAMPLES OF APPLICATION

Example 1

In 100 parts of isoproylated naphthalene was dissolved 5 parts of 3-N-ethyl-N-butylamino-6-methyl-7-(2,3-xylidino)fluoran (obtained in Example of Synthesis 1).

The resultant solution was emulsified by addition of a solution of 25 parts of pigskin-gelatin having an isoelectric point of 8 and 25 parts of gum arabic in 350 parts of warm water (50° C.).

The emulsion was stirred with 1000 parts of warm water added thereto, and the resultant mixture adjusted to pH 4 by addition of acetic acid. It was then cooled to 10° C. and addition of 10 parts of 25% glutaraldehyde aqueous solution perfected the capsulation. The liquid containing capsules thus obtained was applied to one side of the surface of a base sheet of 45 g/m² in weight in an amount of 5 g/m² on a dry basis. To the other side of the surface of the base sheet a dispersion of 20 parts of zinc 3,5-di(α-methylbenzyl)salicylate, 80 parts of kaolin and 30 parts of styrene-butadiene copolymer emulsion (solid content: 50%) respectively being present dispersed in 200 parts of water was applied in the weight of 5 g/m² on a dry basis and dried to thereby obtain a pressure sensitive recording sheet (middle sheet).

Proceeding in such a way that the capsule coated layer be situated to face the acceptor coated layer several of the pressure sensitive recording sheets were compiled, and when exposed to pressure by the tip of a writing utensil a record image of a black color instantaneously appeared on the surface of the acceptor coated layer. It has been ascertained for this pressure sensitive recording sheet that the color development was instantaneous with high speed and high density from the time when it was exposed to the pressure. Further, for this pressure sensitive recording sheet it has been ascertained that the record image as it appeared was maintained unchanged retaining its initial color without occurrence of a discoloration for a long period of time even when exposed to sunlight.

Example 2

In 200 parts of 1% polyvinyl alcohol aqueous solution were added 200 parts of cuprous iodide and 10% sodium sulfite aqueous solution. The mixture was passed through a sand mill and pulverized to an average size of 2 microns. The pulverized material was dispersed in a mixture of 8 parts of polyacrylate emulsion and 20 parts of titanium dioxide and the resultant dispersion was applied to a base sheet of 50 g/m² in weight in an amount of 7 g/m² on a dry basis. To the coated layer on the base sheet the coating composition prepared in Example of Comparative Test (1) wherein 3-N-methyl-N-propylamino-6-methyl-7-(2,4-xylidino)fluoran (obtained in Example of Synthesis 2) was used, was applied in the weight of 5 g/m² on a dry basis to obtain an electrothermal sensitive recording sheet. When the electrothermal sensitive recording sheet was used in a cylindrical scanning recording machine whereby to record an image thereon at a needle pressure of 10 g/cm² and with a scanning speed of 630 mm/sec., the image which appeared was of a black color.

It has been ascertained that the record image was excellent in light resistance and maintained unchanged retaining its initial color without occurrence of discoloration for a long period of time even when exposed to sunlight.

Example 3

In 100 parts of isopropylated naphthalene was dissolved 5 parts of 3-N,N-dibutylamino-6-methyl-7-(2,3-xylidino)fluoran (obtained in Example of Synthesis 5).

The resultant solution was emulsified by addition of a solution of 25 parts of pigskin-gelatin having an isoelectric point of 8 and 25 parts of gum arabic in 350 parts of warm water (50° C.).

The emulsion was stirred with 1000 parts of warm water added thereto, with the resultant mixture adjusted to pH 4 by addition of acetic acid. It was then cooled to 10° C. and addition of 10 parts of 25% glutaraldehyde aqueous solution perfected the capsulation. The liquid containing capsules thus obtained was applied to one side of the surface of a bace sheet of 45 g/m² in weight in an amount of 5 g/m² on a dry basis. To the other side of the surface of the base sheet a dispersion of 20 parts of zinc 3,5-di(α-methylbenzyl)-salicylate, 80 parts of kaolin and 30 parts of styrene-butadiene copolymer emulsion (solid content: 50%) respectively being present dispersed in 200 parts of water was applied in the weight of 5 g/m² on a dry basis and dried to thereby obtain a pressure sensitive recording sheet (middle sheet).

Proceeding in such a way that the capsule coated layer be situated to face the acceptor coated layer several of the pressure sensitive recording sheets were compiled, and when exposed to pressure by the tip of a writing utensil a record image of black color instantaneously appeared on the surface of the acceptor coated layer.

It has been ascertained for this pressure sensitive recording sheet that the color development was instantaneous with high speed and high density from the time when it was exposed to the pressure. Further, for this pressure sensitive recording sheet, it has been ascertained that the record image as it appeared was maintained unchanged retaining its initial color without occurrence of discoloration for a long period of time even when exposed to sunlight.

Example 4

In 200 parts of 1% polyvinyl alcohol aqueous solution were added 200 parts of cuprous iodide and 10% sodium sulfite aqueous solution. The mixture was passed through a sand mill and pulverized to an average size of 2 microns. The pulverized material was dispersed in a mixture of 8 parts of polyacrylate emulsion and 20 parts of titanium dioxide and the resultant dispersion was applied to a base sheet of 50 g/m$^2$ in weight in an amount of 7 g/m$^2$ on a dry basis. To the coated layer on the base sheet the coating composition, which was prepared in Example of Comparative Test (1) wherein 3-N,N-dibutylamino-6-methyl-7-(2,4-xylidino)fluoran (obtained in Example of Synthesis 6) was used, was applied in the weight of 5 g/m$^2$ on a dry basis to obtain an electrothermal sensitive recording sheet. When the electrothermal sensitive recording sheet was used in a cylindrical scanning recording machine to record an image thereon at a needle pressure of 10 g/cm$^2$ and with a scanning speed of 630 mm/sec., the image which appeared was of a black color.

It has been ascertained that the record image was excellent in light resistance and maintained unchanged retaining its initial color without occurrence of discoloration for a long period of time even when exposed to sunlight.

Example 5

In 100 parts of isopropylated naphthalene was dissolved 5 parts of 3-N,N-dibutylamino-6-methyl-7-orthoethylanilinofluoran (obtained in Example of Synthesis 12).

The resultant solution was emulsified by addition of a solution of 25 parts of pigskin-gelatin having an isoelectric point of 8 and 25 parts of gum arabic in 350 parts of warm water (50° C.).

The emulsion was stirred with 1000 parts of warm water added thereto, with the resultant mixture adjusted to pH 4 by addition of acetic acid. It was then cooled to 10° C. and addition of 10 parts of 25% glutaraldehyde aqueous solution perfected the capsulation. The liquid containing capsules thus obtained was applied to one side of the surface of a base sheet of 45 g/m$^2$ in weight in an amount of 5 g/m$^2$ on a dry basis, to the other side of the surface of the sheet base a dispersion of 20 parts of zinc 3,5-di(α-methylbenzyl)salicylate, 80 parts of kaolin and 30 parts of styrene-butadiene copolymer emulsion (solid content: 50%) respectively being present dispersed in 200 parts of water was applied in the weight of 5 g/m$^2$ on a dry basis and dried to thereby obtain a pressure sensitive recording sheet (middle sheet).

Proceeding in such a way that the capsule coated layer be situated to face the acceptor coated layer, several of the pressure sensitive recording sheets were compiled, and when exposed to the pressure of the tip of a writing utensil a record image of black color instantaneously appeared on the surface of the acceptor coated layer.

It has been ascertained for this pressure sensitive recording sheet that the color development was instantaneous with high speed and high density from the time when it was exposed to the pressure. Further, for this pressure sensitive recording sheet, it has been ascertained that the record image as appeared was maintained unchanged retaining its initial color without occurrence of discoloration for a long period of time even when exposed to sunlight.

Example 6

In 200 parts of 1% polyvinyl alcohol aqueous solution were added 200 parts of cuprous iodide and 10% sodium sulfite aqueous solution. The mixture was passed through a sand mill and pulverized to an average size of 2 microns. The pulverized material was dispersed in a mixture of 8 parts of polyacrylate emulsion and 20 parts of titanium dioxide and the resultant dispersion was applied to a base sheet of 50 g/m$^2$ in weight in an amount of 7 g/m$^2$ on a dry basis. To the coated layer on the base sheet the coating composition, which was prepared in Example of Comparative Test (2) wherein 3-N,N-dibutylamino-6-methyl-7-orthoethylanilinofluoran (obtained in Example of Synthesis 12) was used, was applied in the weight of 5 g/m$^2$ on a dry basis to obtain an electrothermal sensitive recording sheet. When the electrothermal sensitive recording sheet was used in a cylindrical scanning recording machine to record an image thereon at a needle pressure of 10 g/cm$^2$ and with a scanning speed of 630 mm/sec., the image which appeared was of a reddish black color.

It has been ascertained that the record image was excellent in light resistance and maintained unchanged retaining its initial color without occurrence of discoloration for a long period of time even when exposed to sunlight.

What is claimed is:

1. A fluoran compound of the formula:

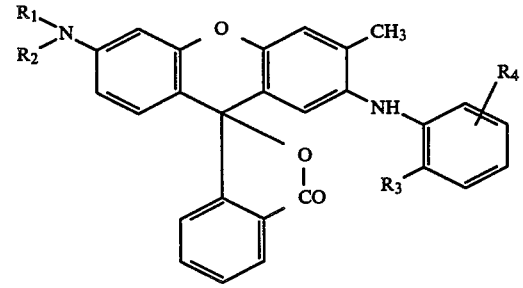

wherein $R_1$ is propyl or butyl, $R_2$ is an alkyl of from one to four carbon atoms, $R_3$ is methyl or ethyl, and $R_4$ is hydrogen or methyl.

2. A fluoran compound according to claim 1, said compound being selected from the group consisting of 3-N-ethyl-N-butylamino-6-methyl-7-(2,3-xylidino)fluoran, 3-N-methyl-N-propylamino-6-methyl-7-(2,4-xylidino)fluoran, 3-N-ethyl-N-butylamino-6-methyl-7-orthotoluidinofluoran, 3-N-ethyl-N-butylamino-6- methyl-7-(2,5-xylidino)fluoran, 3-N,N-dibutylamino-6-methyl-7-(2,3-xylidino)fluoran, 3-N,N-dibutylamino-6-methyl-7-(2,4-xylidino)fluoran, 3-N,N-dibutylamino-6-methyl-7-(2,5-xylidino)fluoran, 3-N,N-dipropylamino-6-methyl-7-(2,3-xylidino)fluoran, 3-N,N-dibutylamino-6-methyl-7-orthoethylanilinofluoran, 3-N-ethyl-N-butylamino-6-methyl-7-orthoethylanilinofluoran, 3-N,N-dipropylamino-6-methyl-7-orthoethylanilinofluoran, 3-N,N-dipropylamino-6-methyl-7-orthotoluidinofluoran, 3-N,N-dibutylamino-6-methyl-7-orthotoluidinofluoran and 3-N,N-dipropylamino-6-methyl-7-(2,4-xylidino)fluoran.

* * * * *